United States Patent
Paturel et al.

(10) Patent No.: US 6,875,580 B2
(45) Date of Patent: Apr. 5, 2005

(54) ANTIBODIES SPECIFIC FOR PLASMACYTOID DENDRITIC CELLS

(75) Inventors: Carine Paturel, Marcy l'Etoile (FR); Giorgio Trinchieri, Charly (FR); Jean-Jacques Pin, St. Bonnet de Mure (FR)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/764,718

(22) Filed: Jan. 26, 2004

(65) Prior Publication Data

US 2004/0166108 A1 Aug. 26, 2004

Related U.S. Application Data

(60) Provisional application No. 60/443,244, filed on Jan. 28, 2003.

(51) Int. Cl.[7] .......................... C07K 16/28; C12N 5/20; G01N 33/543; G01N 33/553; G01N 33/567
(52) U.S. Cl. .......................... 435/7.24; 435/2; 435/7.21; 435/70.21; 435/332; 435/343; 435/343.1; 436/503; 436/512; 436/518; 436/526; 436/548; 530/388.2; 530/388.7; 530/388.73
(58) Field of Search .......................... 435/2, 7.21, 7.24, 435/452, 70.21, 449, 332, 343, 343.1; 436/501, 503, 518, 526, 548, 512; 530/388.2, 388.7, 388.73

(56) References Cited

PUBLICATIONS

Nakano et al., 2001. CD11c+B220+Gr–1+ cells in mouse lymp nodes and spleen display characteristics of plasmacytoid dendritic cells. Journal of Experimental Medicine 194: 1171–1178.*

Asselin–Paturel et al., 2003. Mouse strain differences in plasmacytoid dendritic cell frequency and function revealed by a novel monoclonal antibody. Journal of Immunology 171: 6466–6477.*

* cited by examiner

*Primary Examiner*—Christopher L. Chin
*Assistant Examiner*—James L. Grun
(74) *Attorney, Agent, or Firm*—Michael G. Biro

(57) ABSTRACT

The invention provides immunological reagents (antibodies) capable of binding to plasmacytoid dendritic cells (pDC), to cell lines which express such antibodies and to a process for identifying and purifying plasmacytoid dendritic cells from tissues containing pDC using such antibodies.

6 Claims, No Drawings

ANTIBODIES SPECIFIC FOR PLASMACYTOID DENDRITIC CELLS

CROSS-REFERENCE TO RELATED APPLICATIONS

This application claims priority to U.S. Provisional Application No. 60/443,244, filed Jan. 28, 2003, which is incorporated herein by reference.

FIELD OF THE INVENTION

The invention provides immunological reagents (antibodies) capable of binding to plasmacytoid dendritic cells (pDC), to cell lines which express such antibodies and to a process for identifying and purifying plasmacytoid dendritic cells from tissues containing pDC using such antibodies.

BACKGROUND OF THE INVENTION

Dendritic cells (DC) are antigen-presenting cells (APC) that initiate T cell-dependent immune responses (Steinman, 1991, Ann. Rev. Immunol. 9:271–296). In humans, plasmacytoid DC (pDC) are a DC subset characterized by their ultrastructural resemblance to Ig-secreting plasma cells (Grouard et al., 1997, J. Exp. Med. 185(6):1101–1111), their unique surface phenotype (CD4+IL-3R++CD45RA+HLA-DR+) (Grouard et al., 1997, J. Exp. Med. 185(6):1101–1111; Facchetti et al., 1999, Histopathology 35(1):88–9; Res et al., 1999, Blood 94 (8):2647–57), and their ability to produce high levels of IFNα in response to virus stimulation or to oligodeoxynucleotides (ODN) containing particular CpG motifs (Siegal et al., 1999, Science 284(5421):1835–7; Kadowaki et al., 2001, J Immunol 166(4):2291–5) and induce potent in vitro priming and Th-1 polarization of naive T cells following viral encounter (Cela et al., 2000, Nat Immunol 1(4):305–10; Kadowaki et al., 2000, J Exp Med 192 (2):219–26). pDC are believed to be derived from a precursor common with T cells and B cells (Grouard et al., 1997, J. Exp. Med. 185, 6:1101–1111; Res et al., 1999. Blood 94, 8:2647–57; Res et al., 1999, Blood 94 (8):2647–57; Bruno et al., 1997, J. Exp. Med. 185:875–884; Bendriss-Vermare et al., 2001, JCI 107 :835; Spits et al., 2000, J. Exp. Med. 192 (12):1775–84).

In the mouse, pDC have been recently identified by several groups as CD11c$^{low}$B220$^{hi}$Gr1$^{low}$ cells, able to produce type I IFN in response to viral stimulation and exhibiting plasmacytoid morphology (Nakano et al., 2001, J. Exp Med, 194(8):1171–8 ; Paturel et al., 2001, Nat Immunol. 2(12):1144–1150; Bjorck, 2001, Blood 98(13):3520–6). Mouse pDC can also be obtained in large number in vitro, by differentiating bone marrow cells into dendritic cells in the presence of FLT3L.

In addition to their morphology, their IFNα production and their putative origin, pDC also differ from myeloid DC in their weak phagocytic activity (Grouard et al., 1997, J. Exp. Med. 185, 6:1101–1111), their weak IL-12 production capacity (Rissoan et al., 1999, Science 283:1183–1186), and the signals inducing their activation (Kadowaki et al., 2001, J. Immunol 166(4):2291–5). While recruitment of activated pDC should initiate immunity through naive T cell activation, immature or inactivated DC have been reported to induce immune tolerance, likely through induction of regulatory T cells (Jonuleit et al., 2001, Trends Immunol. 22:394; Bell et a., 2001, Trends Immunol 22:11, Roncarolo et al., 2001, JEM 193:F5; Jonuleit et al., 2000, JEM 162:1213). Moreover, pDC have been shown to induce IL-10 secreting T cells (Rissoan et a., 1999, Science 283:1183; Liu et al., 2001, Nature Immunol 2:585) and CD8 regulatory T cells (Gilliet et al., 2002, J. Exp Med. 195(6):695–704). Human natural IFN-producing cells (HuIPC) have also been shown to play an essential role in activating natural killer (NK) cells to kill virus-infected cells (Bandyopadhyay et al., 1986, J. Exp Med 164(1):180–95). Furthermore, pDC have been recently associated with autoimmune diseases, in particular Lupus erythematosus (Farkas et al., 2001, Am. J. Pathol. 159(1)237–43).

Type I interferons (IFN-α, β or ω) are central players in host resistance to viral or microbial infections (Pfeffer et al., 1998, Cancer Res 58(12):2489–99; van den Broek et al., 1995, Immunol Rev 69(8):4792–6). The critical role of pDC in viral infection has been recently demonstrated in vivo, in MCMV and VSV infection models (Dalod et al., 2002, J Exp Med 195(4):517–28; Barchet et al., 2002, J Exp Med 195 (4):507–16). Indeed, in the absence of mouse pDC, the level of IFNα is dramatically decreased in mice infected with MCMV. In that study, the anti-Gr1 treatment used to deplete pDC, could in addition to neutrophils, also possibly deplete a proportion of macrophages and of activated T cells. However, because all these cells do not produce IFN-α in vitro and T or B lymphocytes are not required for in vivo production of IFN-α, these data demonstrated that either the MIPC are the only cells able to produce in vivo type I IFN in response to MCMV infection or that their early production of type I IFN is necessary to initiate the cascade of IFN production from other cell types (Dalod et al., 2002, J Exp Med 195(4): p. 517–28).

In humans, resting pDC have been shown to specifically express BDCA-2 and BDCA-4 (Dzionek, et al., 2000, J. Immunol. 165(11):6037–46). In mouse, no such specific markers have been identified to date. It would be of great benefit to identify new markers specific for mouse pDC, in order to monitor, characterize and isolate pDC and also to study their function in vivo in animal models.

SUMMARY OF THE INVENTION

The present invention fills the foregoing need by providing a binding compound having the binding characteristics of a monoclonal antibody produced by the hybridoma cell line deposited on Jan. 27, 2003 under ATCC Accession No. PTA-4957. In preferred embodiments, the binding composition is an antibody or antibody fragment. Most preferably the monoclonal antibody is monoclonal antibody 120G8 produced by hybridoma ATCC No. PTA-4957.

Also provided is a hybridoma cell line having Accession No. ATCC PTA-4957.

The invention further provides methods for purifying pDC from a sample containing pDC, which method comprises contacting said sample with a 120G8 antibody and then recovering pDC which have bound to said antibody.

Finally, the invention provides a method for identifying pDC from a sample containing pDC comprising the steps of contacting said sample with a 120G8 antibody to form an antibody/pDC complex, and detecting the presence of said antibody/pDC complex to identify the pDC.

DETAILED DESCRIPTION OF THE INVENTION

The present invention is based, in part, on the discovery of an antibody which specifically recognizes pDC in the mouse.

The nature of the T cell response upon presentation of antigen by DC is dependent on the subpopulation of DC involved and the stage of maturation of presenting DC (Steinman et al., 2000, J. Exp. Med. 191(3):411–6). Despite functional plasticity, MDC and pDC are able to polarize the type of the T cell response toward a Th1 or a Th2 response through their capacity to secrete IL-12 or not, respectively (Rissoan et al., 1999, Science 283:1183–1186). The two DC subtypes also make different links between acquired and innate immune responses, with MDC activating both B cells (Dubois et al., 1999, *J. Leukoc. Biol.* 66:224–230) and NK cells (Zitvogel et al., 2002, *J. Exp. Med.* 195(3):F9–14), and pDC producing large amounts of natural IFNs in response to viruses (Liu, Y. J., 2001, *Cell* 106(3):259–62). In view of the lack of specific markers able to recognize pDC, e.g. in the mouse, both resting and activated, the inventors have generated a mAb directed against mouse pDC.

This antibody, which is of the IgG1/κ isotype, has been designated 120G8. The 120G8 antibody is produced by a hybridoma cell line that was generated by the fusion of spleen cells with the murine myeloma cell line SP$_2$O. This hybridoma was deposited on Jan. 27, 2003 under the Budapest Treaty as ATCC Accession No. PTA-4957. The American type Culture Collection ATCC, is located at 10801 University Blvd., Manassas, Va. 20110-2209 in the United States of America. The 120G8 mAb can be used to selectively isolate pDC from total cells. It stains pDC from either ex vivo total cells or in vitro bone marrow-derived DC. It also recognizes pDC originating not only from different organs in the mouse, but also from different mice strains. It can be used in fluorescence activated coil sorter (FACS) studies, immunohistochemistry (IHC) or immunohistofluorescenve (IHF) staining on tissue sections. Because 120G8 mAb recognizes both resting and activated pDC, it is most helpful to study pDC response to activation, in vitro and in vivo. Finally 120G8 mAb injection in vivo depletes mice of pDC, as determined both phenotypically and functionally.

The term "binding compound" as used herein includes antibodies and functional fragments thereof which specifically bind pDC, and which have an epitopic specificity which is the same as or similar to that of the 120G8 mAb described herein. Binding compounds which have an epitopic specificity which is the same as or similar to that of 120G8 mAb can be identified by their ability to compete with 120G8 mAb for binding to pDC.

EXAMPLES

The invention can be illustrated by way of the following non-limiting examples, which can be more easily understood by reference to the following materials and methods.
Mice, Culture Medium and Antibodies:

Specific pathogen-free BALB/cByJ, 129 SvPas, C57Bl/6J, CBA/J, C3H/HeN, DBA/2J, BALB/c-nude female mice, 6–8 weeks of age, were purchased from Charles River (Iffa-Credo, L'Arbresle, France). All mice experiments were performed following protocols approved by the institutional animal committees and in accordance with EEC Council Directive 86/609 as well as institutional animal care and use guidelines.

Primary cells were grown in complete RPMI1640 medium: RPMI 1640 (Life Technologies, Paisley Park, U.K.) supplemented with 10% (v/v) heat-inactivated fetal calf serum (FCS, Life Technologies), 2 mM L-Glutamine (Life Technologies), 80 μg/ml Gentallin (Schering Plough, Union, N.J.), 10 mM Hepes (Life Technologies), 50 μM, β2-mercaptoethanol (Sigma, St Louis, Mo.), at 37° C. in 5% $CO_2$. High density supernatants of hybridoma were produced in DMEM/F12 (Life Technologies), supplemented with, 2 mM L-Glutamine, 80 μg/ml Gentallin. 10% (v/v) horse serum (HS, Life Technologies) was added unless specified. All antibodies were from Pharmingen (San Diego, Calif.), unless otherwise specified.
Tissue Preparation and Cell Depletion:

Mice were killed by $CO_2$ inhalation. Isolated cells were maintained throughout the procedure in PBS-FCS-EDTA: PBS (Life Technologies) supplemented with 5% (v/v) heat-inactivated FCS and 0.5 mM EDTA (Sigma). Blood cells were collected in excess PBS-FCS-EDTA by cardiac puncture immediately after sacrifice. Spleens, thymus, lymph nodes (popliteal or peripheral (pooled inguinal, axillary, and popliteal), peyer's patches were crushed in PBS-FCS-EDTA and passed through a 25G needle. Red blood cells were lysed in $NH_4Cl$ solution (Stem Cell Technologies, Vancouver, BC) for 5 min. Bone marrow cells were flushed out the bones with cold PBS-FCS-EDTA.

For T and B cell depletions, cells were incubated for 30 min at 4° C. with a mixture of anti-CD3 molecular complex (17A2), anti-CD8β (53-5.8), anti-CD19 (1D3) or anti-erythrocyte (TER119) were alternatively used. Cells and goat anti-rat IgG-coated Dynabeads (Dynal, Oslo, Norway) were mixed under continuous agitation for 15 min at 4° C. Beads and attached cells were removed using a Dynal magnet.

CD11c$^+$ cells were purified by positive selection using CD11c$^+$ Microbeads and MiniMacs (Myltenyi Biotec, Bergisch Gladbach, Germany) starting from either total spleen cells, total bone marrow cells or CD19, CD3, CD8β, TER119 depleted cells.

For bone marrow in vitro derived-DC (BM-DC) in FLT3L, isolated bone marrow cells plated at $10^6$ cells/ml in 24-well plates, were incubated for 9 days in complete RPMI1640 medium supplemented with 25 ng/ml recombinant murine FLT3L (R&D systems, Abingdon, U.K.). Medium was renewed every 2–3 days.
Rat Immunisation with Mouse Plasmacytoid DC Mouse spleen cells from BALB/c mice were incubated for 30 min at 4° C. with a mixture of rat mAb including anti-CD3 molecular complex (17A2), anti-CD8β (53-5.8), anti-CD19 (1D3), anti-CD5 (53-7.3), anti-CD11b (M1/70), and anti-erythroc (TER119) then antibody-coated cells were removed using Dynabeads. Depleted cells were stained with rat anti-Ly6G/C (RB6–8C5)-phycoerythrin (PE), hamster anti-CD11c (HL-3)-biotin, and a cocktail of fluorescein isothiocyanate (FITC)-labeled hamster anti-CD3ε (145-2C11), rat anti-CD19 (1D3), anti-CD5 (53-7.3), anti-CD11b (M1/70), and anti-pan NK cells (DX5) for 30 min at 4° C. Cells were then stained with streptavidin-Pe-Cy5 (Dako, Glostrup, Denmark) and sorted as CD11c$^+$Gr1$^+$CD3ε$^-$CD19$^-$CD5$^-$CD11b$^-$DX5$^-$ cells (pDC) using a FACStar plus flow cytometer (Becton Dickinson, Mountain View, Calif.). Sorted cells were washed three times in PBS (Life Technology, Paisley Park, U.K.), resuspended in PBS and frozen at −20° C. until time of injection.

One rat LOU female (Iffa Credo), 4 weeks old, was immunized with sorted pDC. The protocol was the following:

Day 0: intraperitoneal (ip) injection of $10^6$ cells in Complete Freund adjuvant (CFA)

Day 14: ip injection of $10^6$ cells in Incomplete Freund adjuvant (IFA)

Day 21: ip injection of $10^6$ cells in PBS

Day 35: intravenous (iv) injection of $2.10^6$ cells in PBS

Day 38: Rat was killed and spleen was collected.

Spleen cells were fused with the murine myeloma cell line SP2O, using polyethylene glycol-1000 (Sigma). Hybrid cells were plated in 96-well plates and fed with DMEM/F12 supplemented with 10% HS, 2 mM L-Glutamine, 80 μg/ml Gentallin, 1% culture medium additive (CRTS, Lyon, France), $10^{-5}$ M azaserine (Sigma) and $5 \times 10^{-5}$ M hypoxanthine. Supernatants were screened for reactivity with ex vivo isolated spleen cells, bone marrow and splenic CD11c+ dendritic cells. Selected hybridoma were cloned by limiting dilution.

mAb 120G8 was purified from serum free high density supernatants by anion-exchange chromatography on Hiload Q column (Pharmacia Biotech, Uppsala, Sweden) and coupled with Alexa488 and biotin using standard procedures. Ascites were produced in Balb/c-nude mice (Iffa Credo). Ig isotype was determined by ELISA using a rat Ig subtyping kit (Pharmingen, San Diego, Calif.).

FACS Analysis:

For all FACS analysis, cells, maintained in PBS-FCS-EDTA, were first incubated 15 min with anti-CD16/32 unlabelled rat Ab to ensure blocking of Fc receptor, and were then stained with indicated Abs for 30 min at 4° C. Stained cells were analysed with a FACScan flow cytometer. Negative controls were performed with isotype matched rat or hamster Ig. When no PerCpCy5.5 staining was used, auto fluorescent cells were gated out using FL3 channel.

For surface phenotyping of 120G8+ cells, isolated cells were stained with Alexa-488-labeled 120G8, PE-labelled antibodies (anti-CD3ϵ, CD19, DX5, CD11c, CD45R/B220, Ly6C, Ly6G/C (Gr1, RB6–8C5), CD11b, I-$A^d$, H2-$K^d$) and APC-labelled hamster anti-CD11c (HL-3). For staining on BM-DC at the indicated days of culture in FLT3L, cells were stained with 120G8 Alexa488, anti-CD11c-PE, anti-CD11b-PerCpCy5.5 and anti-CD45R/B220-APC. For surface phenotyping of 120G8+ and 120G8− CD11c+ cells in different organs, isolated cells were stained with 120G8-Alexa488, anti-CD45R/B220-PE, anti-Ly6C-biotin and anti-CD11c-APC. Biotinylated anti-Ly6C was revealed with PerCP-Cy5.5 streptavidin (Pharmingen).

For analysis of DC subsets cell frequency in mouse organs, spleen cells maintained in PBS-FCS-EDTA were stained with rat 120G8-Alexa 488, both anti-CD19 and anti-CD3ϵ-PerCPCy5.5, anti-CD11c-APC and anti-CD8α-PE or anti-CD11b-PE. $CD19^+/CD3\epsilon^+$ cells were gated out using FL3 channel for the analysis. Results are shown as the frequency of the indicated cell subsets among total spleen cells.

Cell Activation and Cytokine Production:

For cell activation, indicated cells were cultured in complete RPMI1640 medium (at $10^6$ cells/ml for non sorted cells and at $0.5\times10^6$ cells/ml for sorted cells) in the absence or presence of indicated stimuli. The formaldehyde-inactivated human influenza virus, strain NK/TM/138/00 (kindly provided by N. Kuehn, Aventis Pasteur, Val de Reuil, France) was added to the cultures at a final concentration of 100 hemagglutinin units (HAU) per ml. Phosphorothioate CpG ODNs, (TCA TTG GM MC GTT CTT CGG GGC G) (SEQ ID NO: 1) unless otherwise specified, were purchased from MWGBiotech (Munich, Germany) and used at a final concentration of 10 $\mu$g/ml. Recombinant mouse IFN-α (Hycult Biotechnology, Uden, The Netherlands) was used at the indicated final concentration. Recombinant mouse IFN-γ (R&D) was used at a final concentration of 2 ng/ml.

For cytokine production by 120G8+ cells, spleen cells were incubated for 30 min at 4° C. with a mixture of mAb including anti-CD3 molecular complex, anti-CD8β, anti-CD19 and anti-erythrocyte (TER119) then antibody-coated cells were removed using Dynabeads. Depleted cells were stained with rat 120G8-Alexa488, hamster anti-CD11c (HL-3)-phycoerythrin (PE) for 30 min at 4° C. Cells were then sorted using a FACStar plus flow cytometer (Becton Dickinson), washed and plated in 96-well culture plates with the indicated stimuli for 20–24 h. Supernatants were collected at 20–24h and stored at −20° C. until assayed for IFN-α and IL-12 (p40 or p70) by specific ELISAs (PBL Biomedical Laboratories, New Brunswick, N.J. and R&DSystems respectively).

For 120G8 expression after cell activation, isolated cells were incubated 20–24 h with the indicated stimuli. Stimulated cells were then stained with 120G8-Alexa488, anti-CD11b-PerCpCy5.5 and anti-CD45R/B220-PE for CD11c+ activated cells or 120G8-Alexa488 and indicated mAbs coupled to PE for total spleen cells. For the latter experiment, indicated cells were gated in using FL2 channel.

Immunostaining of 120G8 on Tissue Section:

Spleens were embedded in OCT-compound (Miles) and snap frozen in liquid nitrogen, and stored at −80° C. until further analysis. Eight micrometer thick cryosections were fixed in 80% Acetone (Sigma) at −20° C. for 20 min, dried at room temperature and stored frozen until stained. Sections were rehydrated in PBS (Life Technology). Avidin/Biotin and peroxydase tissue content were neutralized using specific kit (Vector Laboratory, Burlingame, Calif.) and $H_2O_2$ (Sigma) at 0.3% respectively. Sections were blocked with 2% normal mouse serum (Dako, Glostrup, Denmark), and stainings were performed at room temperature. For the in situ distribution of 120G8+ cells in various mouse tissues, sections were stained sequentially with unlabeled 120G8 Ab for 60 min, goat anti-rat coupled to biotin (Jackson Immunoresearch) for 60 min, extravidin coupled to peroxydase (Sigma) for 30 min and revealed with peroxidase substrate (AEC, Sigma). Counterstaining was performed with hematoxylin (Vector Laboratory). For immunohistofluorescence analysis, sections were stained sequentially with unlabeled 120G8 Ab for 60 min, goat anti-rat coupled to Alexa488 (Molecular Probes, Leiden, The Netherlands) for 60 min, 2% rat serum, indicated Abs coupled to biotin and streptavidine-Alexa594 (Molecular Probes).

In Vivo Treatments:

For CpG treatment, 30 $\mu$l per mouse of the cationic liposome preparation (DOTAP, Roche, Mannheim, Germany) was mixed with 5 $\mu$g CpG ODN in 170 $\mu$l PBS in a polystyrene tube for 10 minutes, before injection into the retro-orbital vein of anesthetized mice. Six hour after CpG injection, spleen were collected and prepared for immunostaining.

For 120G8+ cells in vivo depletion, mice were injected i.p. with optimal amount of 120G8 ascites. For FACS analysis of pDC depletion, spleen cells were isolated 24 h after 120G8 injection and stained with anti-Ly6C-FITC, anti-CD45R/B220-PE, anti-CD11c-APC and anti-CD19-PerCpCy5.5 or anti-CD3ϵ-PerCpCy5.5. For experiments evaluating the contribution of 120G8+ cells to cytokine production in vivo after CpG treatment, mice were injected i.p. with 120G8 ascites at day −1 and at the time of CpG treatment. At 6 h after CpG injection, blood was collected by cardiac puncture immediately after sacrifice. Serum was prepared from whole blood by coagulation for 30 min at 37° C. and centrifugation, and sera were frozen until assayed for cytokine contents. Spleen cells were isolated to evaluate the efficiency of depletion by flow cytometry.

EXAMPLE 1

Selection of Monoclonal Antibody 120G8 Reactive Against Mouse pDC

Supernatants from 2400 hybridomas were screened for reactivity with less than 5% of cells of total mouse spleen cell preparations and further screened for reactivity on spleen depleted of $CD3^+$, $CD19^+$, $TER119^+$, $CD11b^+$ cells. Five 96-well plates out of the 25 plates resulting from the fusion were frozen at −80° C. in HS supplemented with 10% DMSO. Two of those 5 plates were unfrozen, fed with complete DMEM F12 as described above and supernatants were screened a second time by FACS staining on total spleen cells (less than 5%). Selected supernatants were assayed for reactivity on both bone marrow and spleen $CD11c^+$ cells. Supernatant from one hybridoma, named 120G8, was found to react only with a major subset of bone marrow $CD11c^+$ cells (60–70%), and a minor CD11clow subset of spleen $CD11c^+$ cells (10–20%). The hybridoma was cloned by limiting dilution. The resulting clone, once selected for a similar reactivity as the parental line, was further cloned by limiting dilution, and selected for the highest reactivity on mouse $CD11c^+$ cells, i.e. the highest ability to produce the Ab (clone 6).

The antibody was produced from both the parental and the clone 6 in ascites and high density supernatants. MAb 120G8 was found to be of IgG1/κ isotype as determined by ELISA. As the 120G8+ cells in the spleen appeared to be also CD11c+B220+Gr1+ cells (formerly defined as mouse pDC) appeared of particular interest, the mAb 120G8 was selected for further studies.

EXAMPLE 2

120G8 mAb is Highly Reactive with Mouse IFN-α Producing Cells [pDC]

The reactivity of 120G8 mAb was further examined on unstimulated spleen cells, using double immunofluorescence studies with 120G8 coupled to Alexa 488 and lineage specific markers. 120G8 Ab stained a small subset of freshly isolated splenic cells that was homogenous in forward and side scatter. This subset did not express TER119 (erythrocyte lineage marker), CD19 (B cell lineage marker), CD3ε (T cell lineage marker) and DX5 (Nk cell lineage marker). All 120G8+ cells were also CD11c$^{low}$, confirming that the Ab stained a subset of splenic DC. These results are representative of at least 3 experiments.

Next, the ability of 120G8 mAb to specifically recognize IFN-α producing cells (IPC) was tested in vitro. CD11c+ splenic cells have already been demonstrated to be the only cells to produce high amounts of IFNα in vitro in response to influenza virus (Paturel et al., Nat Immunol, 2001). CD11 c+120G8+ and CD11c+120G8− cells were purified by flow cytometry from spleen cells depleted of CD3+CD19+CD8β+TER119+ cells. The two subsets were stimulated in vitro by inactivated influenza virus or CpG as described above. Experiment was performed three times and gave similar results. IFN-α and IL-12p40 production from both sorted populations incubated with medium alone were below ELISA detection level. Only the 120G8+ subset of CD11c+ cells produced IFN-α after both influenza virus and CpG stimulation. IFN-α production by 120G8− sorted cells in response to both influenza virus and CpG was very low or below detection levels. 120G8+ cells were also able to produce IL-12p40 in response to both stimuli, but for CpG stimulation, at a lower level than 120G8− cells, a subset that includes CD11c$^{high}$ DC. This is in agreement with previous data showing that CD8α+CD11c$^{high}$ DC are able to produce high amounts of IL-12 in response to various stimuli.

EXAMPLE 3

Surface Phenotype of 120G8+CD11c+ Splenic Cells

Mouse pDC have been previously described to be CD11c+Gr1+B220+ cells in the spleen (Paturel, 2001, Nagano, 2001, Bjorck, 2001), and CD11c+B220+CD11b− cells in DC derived in vitro from bone marrow cells. To study surface phenotype of 120G8+ cells, in comparison with 120G8-CD11c+DC, CD11c+ ex vivo isolated and in vitro-derived DC in FLT3L were stained with 120G8, CD11c and several Abs coupled to PE. When ex vivo isolated splenic CD11c+ cells were analyzed, 120G8+ cells were B220$^{high}$, Gr1$^{low}$, Ly6C$^{high}$, CD11b−, CD8α$^{neg/low}$, IA$^d$ $_{low}$ and H-2K$^{d+}$, whereas CD11c+120G8− cells were B220$^{neg/low}$, Gr1−, Ly6C$^{neg/low}$, CD11b$^{+/−}$, CD8α$^{neg/hi}$, IA$^d$ $_{low/high}$ and H-2K$^{d+}$. 120G8 phenotype fits with the previously described surface phenotype of mouse pDC. Furthermore, 120G8 also stained previously identified CD11b−CD11c+B220+ mouse pDC, derived in vitro in FLT3L-stimulated bone marrow cell cultures (BM-DC). When BM-DC were analyzed, 120G8+ cells were B220$^{high}$, Gr1$^{neg/low}$, Ly6C$^{high}$, CD11b− whereas 120G8− cells were B220$^{neg/low}$, Gr1−, Ly6C$^{neg}$, CD11b+.

Thus, 120G8 mAb stains both mouse splenic pDC and in vitro derived pDC.

EXAMPLE 4

120G8 is an Early Marker of Mouse pDC Differentiation

120G8 mAb staining on BM-DC (FLT3L) was investigated between day 6 and day 10 of pDC differentiation in vitro. Cells were stained with 120G8, CD11c, CD11b and B220. 120G8 mAb did not stain CD11c− cells from day 6 to 10. However, all 120G8+ cells were CD11c+CD11b−B220+ cells as early as after 6 days of culture. A subset of B220+CD11c+120G8− could also be detected, that was CD11b+ and most probably issued from CD11b+ myeloid DC. While percentage of CD11c+ cells increased from day 6 (70%) to 8 (90%), and stayed constant until day 10, the percentage of 120G8+ cells among CD11c+ cells increased slowly from day 6 (23%) to 8 (38%), and rapidly decreased thereafter (4% at day 10). These results demonstrate that 120G8 mAb is an early marker of mouse pDC along their differentiation in vitro.

EXAMPLE 5

Surface Phenotype of 120G8+ Cells in Various Lymphoid Organs

The staining of 120G8 mAb was investigated in spleen, bone marrow, blood, thymus, peripheral and mesenteric lymph node from Balb/c mice. Isolated cells were analyzed in quadruple surface staining with 120G8, anti-CD45R/B220, anti-Ly6C and anti-CD11c Abs. Ly6C and B220 expressions on CD11c+120G8+ and CD11c+120G8− cells was investigated. In all organs tested and in blood, CD11c+120G8+ were all B220$^{high}$Ly6C$^{high}$. In contrast, no CD11c+120G8− were B220$^{high}$Ly$_6$C$^{high}$. This demonstrate that 120G8 mAb can recognize mouse pDC (CD11c+B$_{220}$$^{high}$Ly6C$^{high}$) cells, regardless of which tissue they have been isolated from.

EXAMPLE 6

Frequency of 120G8+ Cells in Different Mice Strains

The ability of 120G8 mAb to react with pDC form different mice strains was further investigate. 120G8 mAb reacted with splenic pDC isolated from BALB/cByJ, 129 SvPas, C57Bl/6J, CBA/J, C3H/HeN and DBA/2J mice. The frequency of 120G8+ DC subset among total spleen cells from those 6 different mice strains was further investigated. Spleen cells were isolated from mice of the same age (3 mice per mice strain, experiment performed twice), and stained with 120G8, CD11c, CD19 and CD3ε. CD19/CD3ε+ cells were gated out for the analysis. Analysis of pDC frequency among total spleen cells showed that it varies depending on which mice strain is considered, e.g. the C57/BI6 mice exhibited the lowest splenic pDC frequency (0.6%+/−0.06 of total spleen cells), and the 129Sv mice the highest frequency (1.94%+/−0.37 of total spleen cells).

EXAMPLE 7

Immunohistochemical Staining of 120G8 on Tissue Section

The in situ distribution of 120G8+ cells was examined by immunohistochemical analysis of thymus, spleen, peyer's patches, peripheral lymph node, mesenteric lymph node. In all these organs, 120G8+ individual cells could be detected. In some organs (e.g. thymus), some low staining on endothelial cells could be detected. Some low staining on intestinal villosity was also detected.

EXAMPLE 8

120G8 is Maintained on Mouse pDC after in Vitro Activation

BDCA2, CD123, BDCA4 are three markers commonly used to detect pDC in humans. However it is known that activated human pDCs down-regulate these markers very rapidly in vitro. Thus it has been to date very difficult to detect activated pDC in situ. In mouse the pDC (resting or activated) are commonly detected by double staining with anti-CD11c and anti-CD45R/B220, but this combination stains other cells, e.g. B cells. In order to evaluate 120G8 staining on resting and on activated pDC, MACS purified CD11c+ splenic cells from 129Sv mice were incubated in vitro for 20 h with or without inactivated Influenza virus and CpG ODN 1668 (TCC ATG ACG TTC CTG ATG CT) (SEQ ID NO: 2). The mean fluorescence intensity of 120G8 mAb staining stayed constant on a small CD11c$^+$B220$^{high}$CD11b$^-$ subset (pDC), in all conditions tested. Although some CD11c$^+$B220$^{hi}$120G8$^-$ were detected after Influenza virus and CpG stimulation, those cells also expressed CD11b, suggesting that some myeloid DC could up-regulate B220, but not 120G8, further confirming the specificity of 120G8 staining on pDC.

In order to further confirm that 120G8 mAb can also stain activated pDC in vivo, 129Sv mice were treated with CpG as described in methods. Spleen cells were isolated 6 h after CpG injection, and activation markers, expressed on DC, were studied on DC subsets. 120G8+ cells were upregulating DC activation molecules such as CD40, CD86, and to a lesser extent CD8α and MHC class II molecules after in vivo stimulation with CpG. Those cells showed the same level of CD11c (low) and CD11b (negative) in control and CpG treated mice, and the mean fluorescence intensity of 120G8 staining in pDC stayed constant. Thus 120G8 mAb recognizes resting and activated pDC, both in vitro and in vivo.

EXAMPLE 9

120G8+ Cells Localisation in Spleen from Normal and CpG Activated Mice

While some studies have shown that human pDC are located in the T cell zone, the cells producing IFNα in response to HSV infection have been located in the splenic marginal zone in the mouse (Eloranta, Alm, Scand J Immunol, 1999). Immunohistochemical staining studies, as presented in example 7 suggested that splenic pDC in normal mice were located in the T cell zone. As 120G8 mAb appears as a unique tool to stain both resting and activated pDC in situ, we treated 129Sv mice with CpG as described in methods, in order to follow mouse pDC localisation in spleen. This study was performed by immunofluorescence in situ analysis, with costaining in the spleen, 6 h after CpG treatment, of 120G8+ cells in green fluorescence (Alexa488 fluorochrome) and T, B, DC or macrophages in red fluorescence (Alexa594 fluorochrome, with anti-CD3ε, anti-CD19, anti-CD11c (N418 clone) and anti-CD11b mAbs). It should be noted that 120G8+ cell could not be stained by CD11c under our experimental conditions, due to the low expression of CD11c by pDC. Thus only CD11c $^{high}$ were detected by CD11c in situ staining. Serial sections were analyzed for CD19, CD3 or CD11b co-staining with 120G8. In resting animals, 120G8 mAb stained cell from both the T cell zone (CD3□ staining) and the marginal zone (CD11b staining). No 120G8+ cells could be found in the B cell zone (CD19 staining). CD11c$^{high}$ cells (CD11c staining) were detected in the bridging channel between red pulp and the T cell zone, but did not show the same pattern of distribution as pDC.

In CpG activated spleen, 120G8 mAb stains cell from the marginal zone. No or few 120G8+ cells could be detected in the B or T cell zone. In contrast, a massive influx of CD11c$^{high}$ cells could be detected in the T cell zone.

Thus, 120G8 mAb can be used to follow pDC migration in response to activation, directly in situ.

EXAMPLE 10

In Vivo Depletion of 120G8 Cells Abrogates IFN-α Production

In previous studies, the role of pDC in viral infections has been demonstrated by depleting those cells with anti-Ly6G/C (Gr1) treatment. This treatment, in addition to pDC and neutrophils, also possibly depletes a proportion of macrophages and of activated T cells. Thus the use of 120G8 to deplete specifically pDC could be of a great use for in vivo studies. BALB/c mice were injected i.p. or not with 120G8 mAb and 24 h later, spleen cells were isolated for FACS analysis of Ly6C+B220+CD11c+ frequency in spleen cells, as well as the level of CD19 or CD3ε contaminating cells, both in non treated and 120G8 treated mice (3 mice per group). In vivo treatment with 120G8 Ab decreased the frequency of splenic Ly6C$^+$B220$^+$CD11c$^+$ cells. Furthermore, the remaining Ly6C$^+$B220$^+$CD11c$^+$ cells were not all pDC, since they expressed CD3□□(42%) and to a lesser extent CD19 (18%).

To assess the effect of 120G8 depletion on IFNα production, seric IFNα and IL12 production was assayed 6 h after CpG treatment in 129Sv mice (3 mice per group), previously depleted of 120G8+ cells or not. Control mice sera (DOTAP alone) were negative for both cytokines. 120G8 treatment completely abolished IFNα production induced by CpG treatment (13300 pg/ml+/−1500 for normal mice, less than 150 pg/ml for 120G8 treated mice), while resulting in a small inhibition of IL12 production, both p40 and p70 (IL-12p70:1240 pg/ml+/−540 for normal mice, 300 pg/ml+/−74 for 120G8 treated mice; IL-12p40:5806 pg/ml+/−1135 for normal mice, 4250 pg/ml+/−1170 for 120G8 treated mice). Thus 120G8 mAb can be used to deplete mice from IFNα producing cells in vivo.

EXAMPLE 11

120G8 Expression is Up-Regulated on B Cells in the Presence of IFNα

120G8 mAb stains only pDC among total resting cells isolated from normal mice. We investigated whether some other cells could also be stained by 120G8 after cytokine activation. Spleen cells were isolated from Balb/c mice and incubated 24 h in the presence of cytokines. Double staining with 120G8 and anti-CD19, CD4, CD8β or CD11c mAbs was then analyzed on these cells. Autofluorescent cells were gated out using FL3 channel. This demonstrated that the antigen recognized by 120G8 mAb was upregulated on B cells and CD11c+ DC in response to IFN-α at 100 U/ml, but not on T CD4+ or on T CD8+ DC. This up-regulation was not observed in response to IFNγ, IL-12 or TNFα. However the mean fluorescence intensity of 120G8 staining on B cells still remained at least one log lower than on pDC.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A hybridoma cell line deposited as ATCC Accession No. PTA-4957.

2. An antibody produced by the hybridoma cell line of claim 1.

3. The antibody of claim 2, wherein said antibody is a monoclonal antibody.

4. An antigen binding fragment of the antibody of claim 2.

5. A method for purifying murine plasmacytoid dendritic cells from a sample, said method comprising the steps of contacting said sample with the antibody of claim 2, and recovering said cells that are bound to said antibody.

6. A method for identifying murine plasmacytoid dendritic cells from a sample, said method comprising the steps of contacting said sample with the antibody of claim 2 to form an antibody/plasmacytoid dendritic cell complex, and detecting said complex.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: oligodeoxynucleotide (ODN)

<400> SEQUENCE: 1
tcattggaaa acgttcttcg gggcg                                    25

<210> SEQ ID NO 2
<211> LENGTH: 20
<212> TYPE: DNA
<213> ORGANISM: Artificial Sequence
<220> FEATURE:
<223> OTHER INFORMATION: oligodeoxynucleotide (ODN)

<400> SEQUENCE: 2
tccatgacgt tcctgatgct                                          20